United States Patent [19]
Addor

[11] 3,966,959

[45] June 29, 1976

[54] INSECTICIDAL AND ACARICIDAL PYRETHROID COMPOUNDS

[75] Inventor: Roger Williams Addor, Pennington, N.J.

[73] Assignee: American Cyanamid Company, Stamford, Conn.

[22] Filed: Feb. 13, 1975

[21] Appl. No.: 550,105

[52] U.S. Cl. ............................ 424/304; 260/464; 260/465 D; 260/468 G; 260/473 F; 424/305; 424/306; 424/308
[51] Int. Cl.$^2$ ............................................ A01N 9/20
[58] Field of Search ............ 260/468 G, 473 F, 464, 260/465 D; 424/304, 306, 308, 305

[56] References Cited
UNITED STATES PATENTS

| | | | |
|---|---|---|---|
| 3,647,857 | 3/1972 | Morgan............................ | 424/306 X |
| 3,823,177 | 7/1974 | Fanta et al....................... | 260/468 G |
| 3,835,176 | 9/1974 | Matsuo et al.................... | 424/306 X |

FOREIGN PATENTS OR APPLICATIONS 820,418   3/1975   Belgium

*Primary Examiner*—Leonard Schenkman
*Attorney, Agent, or Firm*—H. G. Jackson

[57] ABSTRACT

This invention relates to novel m-phenoxybenzyl esters of spirocarboxylic acids which are useful as topical insecticidal and acaricidal agents for treatment of homothermic animals, and as insecticidal agents effective for the protection of agricultural crops, harvested cereals, and the like.

16 Claims, No Drawings

INSECTICIDAL AND ACARICIDAL, PYRETHROID COMPOUNDS

CROSS REFERENCE TO RELATED APPLICATION

Michael S. Schrider's copending application Ser. No. 550,106 filed of even date discloses a method for the systemic control of ectoparasites wherein compounds of the invention of this application are administered to homothermic animals.

BACKGROUND OF THE INVENTION

1. Field of the Invention

The field of the invention is new pyrethroids useful for control of pests.

2. The Prior Art

Pyrethrin-like compounds (pyrethroids) are known in the chemical art. Many such compounds have been shown to possess insecticidal properties, but most have failed to provide entirely satisfactory insect and/or acarina control. None, to the best of our knowledge, has been suggested for the control of soil-borne insects and, with few exceptions, all have been subject to extremely rapid degradation to non-toxic substances. This latter property has been recognized in the past as a major deficiency of the pyrethroids. While such compounds have provided excellent knockdown of insects, rapid degradation of said compounds has resulted in lack of residual insect control even for a few days.

In this regard, it is well-known that pyrethrins and synthetic pyrethroids are generally too unstable to air and light to be useful for the control of agronomic and forest insects [Y. L. Chen and J. E. Casida, J. Agr. Food Chem., 17, 208(1969)]. Although this rapid degradation may be desirable for environmental reasons, it is of course obvious that there must be sufficient residual presence of the toxicant to ensure economic control of a particular pest.

To this end, a great deal of effort has been expended in attempting to effect sufficient stabilization of existing materials, through the use of light absorbers and antioxidants, to allow their useful application, e.g. see R. P. Miskus and J. S. Andrews, J. Agr. Food Chem., 20, 313(1972).

Another approach to the development of highly active effective pyrethroid insecticides has involved a search for molecular types which retain a high degree of insecticidal activity typical of the best pyrethroids while introducing sufficient stability to air and light to ensure their applicability in the field. An apparent success in this effort is the recent discovery by Elliott and coworkers of the compound m-phenoxybenzyl ($\pm$)-cis, trans-2,2-dimethyl-3(2,2-dichlorovinyl)cyclopropane carboxylate [M. Elliott et al., Nature 246, 169(1973)]. The improved stability of this compound (permethrin) has resulted in part from the replacement of the oxidatively susceptible dimethylvinyl side-chain on the cyclopropane ring of chrysanthemic acid by a dichlorovinyl substituent. Such an improvement might indeed have been anticipated based on Chen and Casida's earlier work. However, the fortuitous combination of improved stability and high degree of insecticidal activity found by Elliott was unexpected.

We have now discovered a new series of esters which, in addition to showing an amazing degree of insecticidal activity, are unexpectedly stable on plant surfaces. This sought for but most difficult to find combination of activity and stability result from novel esters of the type described herein.

Unlike permethrin, these compounds do not rely on replacement of essential methyl groups by chlorine atoms to effect greater stability. Indeed, no atoms other than carbon, hydrogen, and oxygen are present. Thus it is surprising that the esters of this invention are not susceptible to the immediate light-promoted oxidative degradation which limits the agronomic effectiveness of most of the pyrethroids disclosed to date.

It is, therefore, an object of the present invention to provide pyrethroid compounds which are highly effective insecticidal compounds and which are not subject to immediate degradation, but provide insect control for from several days to several weeks before they are detoxified.

It is also an object of this invention to provide pyrethroid compounds which are useful as contact and/or stomach poisons effective for protecting important agronomic crops, such as cotton, soybeans, tobacco, alfalfa, corn, cole crops, leafy vegetables, snapbeans and tomatoes, from attack by insects, particularly *Lepidopterous*, *Homopterous* and *Colepterous* insects.

The importance of these insects is evidenced by the fact that in 1973 the cotton boll weevil, *Anthonomus grandis* (Boheman) and the tobacco budworm, *Heliothis virescens* (Fabricius) were two species important among the cotton insect complex which required control measures involving 45 million treatment acres. For soybeans and snapbeans, sprays were made to control a complex of insects which included the Mexican bean beetle, *Epilachna varivestis* Mulsant and the black bean aphid, *Aphis fabae* (Scopoli) involving over 5 million treatment acres; and the cabbage looper, *Trichoplusia ni* (Huber) was a major member of an insect complex which attacked sweet corn, cole crops, leafy vegetables and tomatoes and required insecticide treatment of an additional 8 million acres of crops.

While many pyrethroids exhibit some insecticidal properties there are, nevertheless, many insects such as those mentioned above which are not adequately controlled by the pyrethroids presently available. Advantageously, the compounds of the present invention are insecticidal and, more importantly they are pyrethroids which are effective for the control of the above indicated boll weevil, budworm, Mexican bean beetle, aphid and cabbage looper, complex, which ravage cotton, tobacco, soybeans, alfalfa, corn, cole crops, leafy vegetables, snapbeans and tomatoes.

It is a further object of this invention to provide pyrethroids which are highly effective soil insecticidal agents.

It is also an object of this invention to provide pyrethroids which are highly effective topical insecticidal and acaricidal agents useful for the treatment of warmblooded or homothermic animals.

U.S. Pat. Nos. 3,835,176, issued Sept. 10, 1974 and 3,823,177, issued July 9, 1974. The U.S. Pat. No. 3,835,176 to Matsuo et al. discloses alpha-cyanobenzyl cyclopropanecarboxylates as insecticidal agents. These compounds are effective as stated; however, they are not said to be useful for control of soil insects or exhibit extended residual insecticidal activity. The U.S. Pat. No. 3,823,177 to Fanta et al. relates to insecticidal esters of spirocarboxylic acids. However, like the U.S. Pat. No. 3,835,176, Fanta et al. do not suggest soil insecticidal activity, or extended residual activity.

SUMMARY OF THE INVENTION

The invention is novel phenoxybenzyl esters of spirocarboxylic acids of the formula

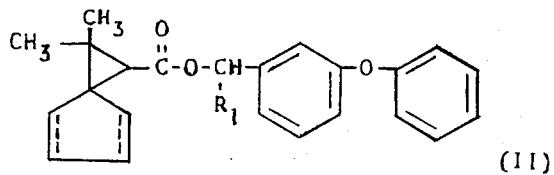

(I)

and

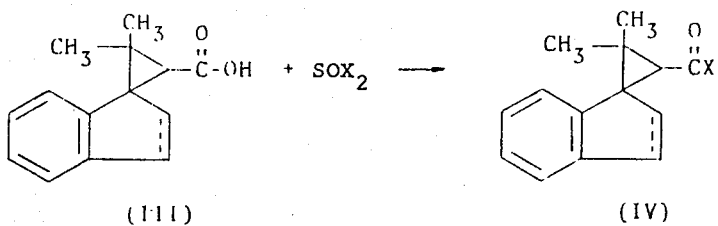

(II)

wherein $R_1$ is hydrogen, cyano or ethylnyl, ═══ represents a single or double bond, and the optical and geometric isomers thereof and a method for the control of insects, including soil-borne insects, by contacting the insects, their habitat or their food supply, with an insecticidally effective amount of a phenoxybenzyl ester of a spirocarboxylic acid represented by formula I or II above.

DETAILED DESCRIPTION

The phenoxybenzyl esters of benzospirocarboxylic acids depicted by formula I, can be prepared by reacting approximately equimolar amounts of an acid halide, preferably the chloride, of a benzospirocarboxylic acid (IV) and a m-phenoxybenzyl alcohol (V). The reaction is generally conducted in the presence of a suitable solvent such as benzene, toluene, diethyl ether, or the like, at a temperature between about 10°C and 30°C, and in the presence of an acid acceptor such as an organic tertiaryamine such as triethylamine, trimethylamine, pyridine, or the like. The reaction can be graphically illustrated as follows:

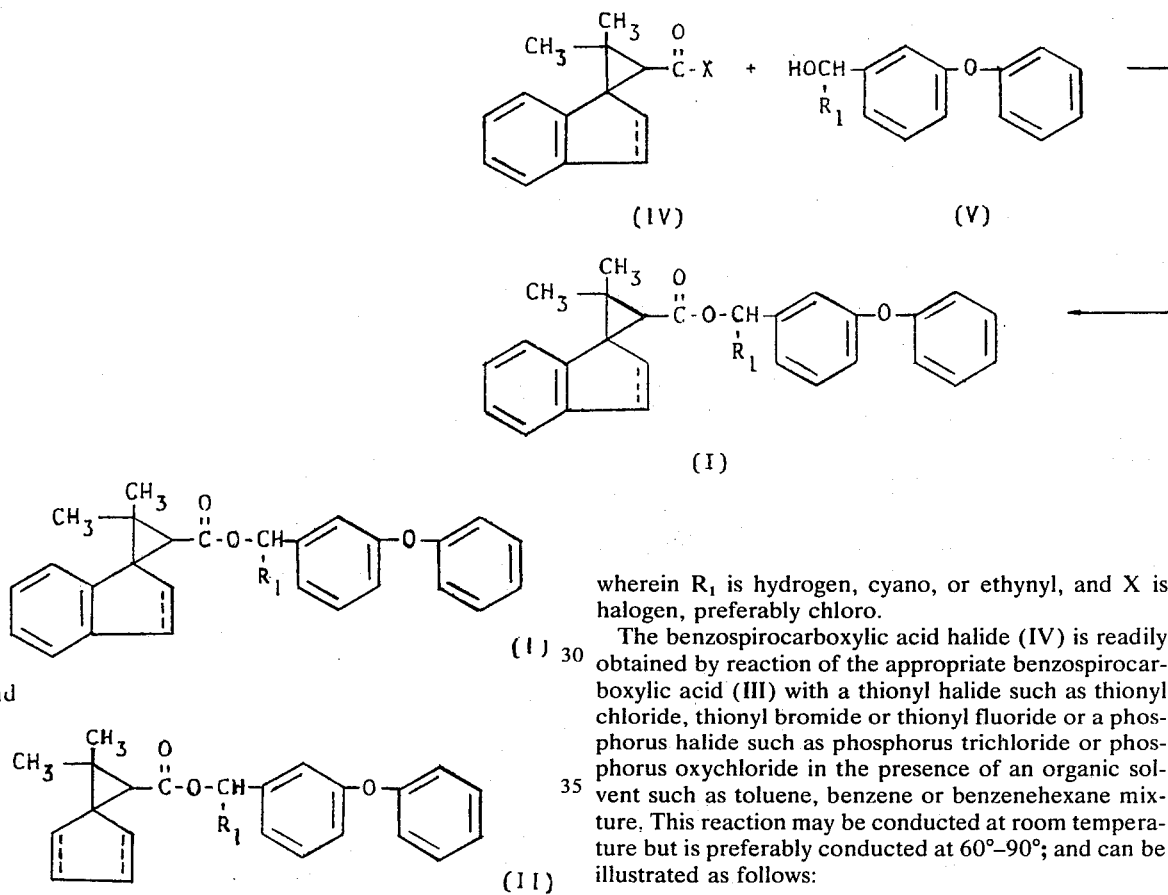

wherein $R_1$ is hydrogen, cyano, or ethynyl, and X is halogen, preferably chloro.

The benzospirocarboxylic acid halide (IV) is readily obtained by reaction of the appropriate benzospirocarboxylic acid (III) with a thionyl halide such as thionyl chloride, thionyl bromide or thionyl fluoride or a phosphorus halide such as phosphorus trichloride or phosphorus oxychloride in the presence of an organic solvent such as toluene, benzene or benzenehexane mixture. This reaction may be conducted at room temperature but is preferably conducted at 60°–90°; and can be illustrated as follows:

The formula II phenoxybenzyl esters of spirocarboxylic acids can be prepared in a manner similar to that described above for the preparation of the formula I benzospiro compounds, by substituting the appropriate spirocarboxylic acid (VI) for the above-mentioned benzospirocarboxylic acid (III); converting said acid to its corresponding acid halide (VII) and reacting the thus-formed acid halide with m-phenoxybenzyl alcohol (V), under the conditions mentioned above, to obtain the formula (II) m-phenoxybenzyl ester of the spirocarboxylic acid. This reaction can be graphically illustrated as follows:

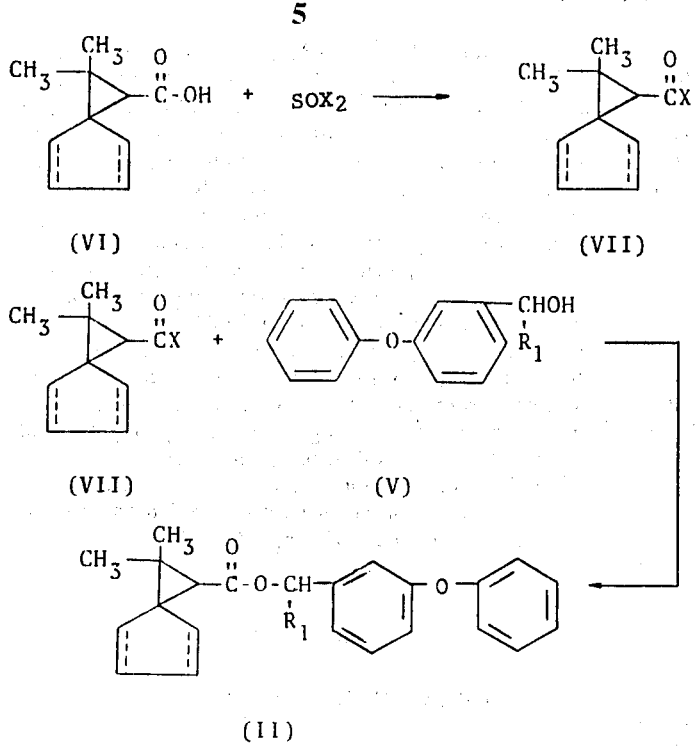

wherein X is halogen, preferably chloro, and $R_1$ is hydrogen, cyano, or ethynyl.

In accordance with this invention, it should also be understood that various geometric isomers as well as optical isomers of the above-identified compounds do result from the preparations described. For example, in the synthesis of the 2,2-dimethylspiro[2,4]hepta-4,6-diene-1-carboxylic and 2,2-dimethylspiro[2,4]hepta-4-ene-1-carboxylic acid esters of m-phenoxybenzyl alcohol, $d$ and $l$ isomeric pairs are formed. In the preparation of the α-cyano- and α-ethynyl-m-phenoxybenzyl esters, an additional chiral center is introduced, and this allows for additional $d,l$ pairs. Additionally, the esters derived from 2,2-dimethyl-4,5-benzospiro[2,4-]hepta-4,6-diene-1-carboxylic acid and 2,2-dimethyl-4,5-benzospiro[2,4]hepta-4-ene-1-carboxylic acid will be further complicated by the presence of cis and trans isomers.

These isomers will, of course, vary somewhat in the degree of insecticidal and acaricidal activity which they exhibit toward a given pest; however, they are useful as insecticidal and/or acaricidal agents.

For use as animal systemic insecticidal and acaricidal agents, the compounds of this invention can be administered to the animal host either orally or parenterally. When given orally, it may be in any convenient form designed for oral administration such as a bolus, capsule, tablet or as an oral drench. The active agent may also be incorporated in an edible animal feedstuff such as a nutritionally balanced diet containing from 0.01% to 3.0%, and preferably 0.01% to 1.5% by weight of feed of the active compound.

If desired, the systemic insecticidal and acaricidal agent may be introduced into the body of the animal by subcutaneous, intramuscular or intraperitoneal injection, such that it may be distributed through the animal's body by the action of the animal's circulatory system. In practice, the systemic agent may be dissolved or dispersed in a pharmaceutically acceptable carrier such as water, propylene glycol, vegetable oil, glycerol formal, or the like, for administration.

Advantageously, the systemic agents have relatively low mammalian toxicity and are effective for protecting a variety of animals, particularly livestock and domestic animals such as cattle, sheep, horses, dogs, cats, and the like, from attack by fleas, mosquitoes, flies, ticks, and the like.

For the control of insects, including soil insects, which attack growing plants and/or harvested crops, including stored grain, the insecticidal compounds of this invention may be applied to the foliage of plants, the insect's habitat and/or the insect's food supply. Generally, the active compound is applied in the form of a dilute liquid spray; however, it may also be applied as an aerosol, a dust, wettable powder, or the like.

Liquid sprays which are particularly useful are oil sprays and emulsifiable concentrates which can be further diluted for application.

A typical emulsifiable concentrate useful for protecting a variety of crops such as cereals, cole crops, cucurbits, ornamentals, shrubs, and the like, may comprise about 24% by weight of the active agent; 4% by weight of an emulsifying agent, conventionally employed in the preparation of pyrethroid formulations; 4% by weight of a surfactant; 23% by weight of an organic solvent such as cyclohexanone; and about 45% by weight of a petroleum solvent having a minimum aromatic content of about 93 volume %.

The compounds of this invention are highly effective as contact and stomach poisons for ixodide ticks and for a wide variety of insects, particularly Dipterous, Lepidopterous, Coleopterous and Homopterous insects. Moreover, these compounds are unique pyrethroids, in that they exhibit extended residual insecticidal activity and are surprisingly effective for the control of soil-borne insects. They do not require admixture with a stabilized phenol derivative such as bisphenols, BHT, arylamines, or the like, to achieve insecticidal and acaricidal compositions having stabilized effects; however, they may be used in combination with other biological chemicals, for example, pyrethroid synergists such as piperonyl butoxide, sesamex or n-octyl sulfoxide of isosafrole.

The invention is further demonstrated by the nonlimiting examples provided below.

EXAMPLE 1

Preparation of 2,2-Dimethyl-4,5-benzospiro[2,4]hepta-4,6-diene-1-carboxylic acid, m-phenoxybenzyl ester.

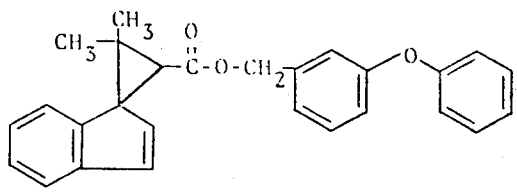

To 4.3 g (0.02 mol) of 2,2-dimethyl-4,5-benzospiro-2,4-hepta-4,6-diene-1-carboxylic acid in either hexane/benzene or benzene is added 8 ml of thionyl chloride. The solution is then stirred for 12 hours at room temperature. The solvent is then removed in vacuo leaving 4.7 g of an orange liquid (theoretical yield). Infrared indicates an acid chloride carbonyl at 1790 cm$^{-1}$.

The acid chloride and 4.0 g (0.02 mol) of m-phenoxy benzyl alcohol are dissolved in 20 ml of ether, and 2.1 g (0.02 mol) of triethylamine dissolved in 8 ml of ether is added dropwise at 20°C. Solids precipitate from solution immediately. The resulting mixture is stirred for 12 hours at room temperature. The crude product is partitioned in an ether/water mixture, and the ether layer is dried over magnesium sulfate and concentrated in vacuo to yield 7.7 g (96% theory) of a brown liquid.

The crude product is purified by dry-column chromatography on silica gel using 25% methylene chloride in hexane as a solvent. 4.4 Grams of a pale yellow liquid is obtained. The infrared spectrum shows an ester carbonyl band at 1720 cm$^{-1}$. The nuclear magnetic resonance spectrum (CCl$_4$) shows the following: $\delta$ = 1.41, 1.45, 1.58, 1.66 (4S, 6H, methyls), 2.61 (S, 1H, cyclopropane H), 4.85–5.10 (m, 2H, O-CH$_2$), 6.12 (d, 0.5H, J = 5.5 Hz, vinyl), 6.66–7.76 (m, 14.5H aromatic and vinyl).

Analyses: Calculated for C$_{27}$H$_{24}$O$_3$: C, 81.83; H, 6.06. Found: C, 82.14; H, 6.29.

EXAMPLE 2

Preparation of 2,2-Dimethyl-4,5-benzospiro[2,4]hepta-4,6-diene-1-carboxylic acid, α-cyano-m-phenoxybenzyl ester.

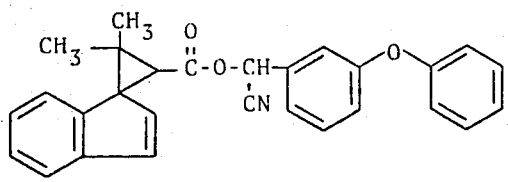

2,2-Dimethyl-4,5-benzospiro[2,4]hepta-4,6-diene-1-carboxylic acid, 3.4 g, is dissolved in 100 ml of a hexane/benzene (4:1) solution. Thionyl chloride, 15.0 g, is then added and the solution is stirred for 12 hours. Refluxing is carried out for 20 minutes, and the volume is reduced in vacuo to remove solvents and excess thionyl chloride. The acid chloride is used directly without further purification. The acid chloride is taken up in 20 ml of benzene and is added dropwise to a solution of 3.1 g of α-cyano-m-phenoxybenzyl alcohol and 1.0 g of pyridine in 100 ml of benzene. After 4 hours, the precipitate is filtered, and the filtrate reduced in vacuo to give a viscous oil. Purification by column chromatography on silica gel with elution by chloroform/hexane (1:2) gives 1.3 g of pale yellow oil which exhibits the following spectral properties: infrared spectrum (neat film) 1730 cm$^{-1}$; nuclear magnetic resonance spectrum (CDCl$_3$) $\delta$ = 6.8–7.6 (m, 14.5H, aromatic and vinyl), 6.37 (m, 1H,

), 6.22 (d, 0.5H, vinyl), 2.73 (m, 1H,

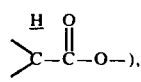), 1.72–1.43 (m, 6H, methyls).

EXAMPLE 3

Preparation of 2,2-Dimethyl-4,5-benzospiro[2,4]hepta-4-ene-1-carboxylic acid, m-phenoxybenzyl ester.

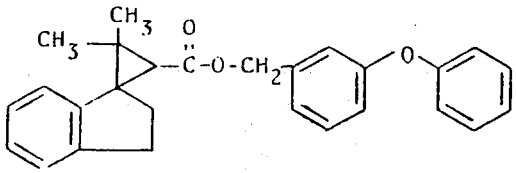

The procedure of Example 1 is followed using 2,2-dimethyl-4,5-benzospiro[2,4]hepta-4-ene-1-carboxylic acid in place of 2,2-dimethyl-4,5-benzospiro[2,4]hepta-4,6-diene-1 carboxylic acid to give the crude product as an oil. The pure ester obtained by chromatography had the following spectral properties: Infrared spectrum (heat film) 1720 cm$^{-1}$; nuclear magnetic resonance spectrum (CCl$_4$)$\delta$ = 6.7–7.6 (m, 13H, aromatic), 4.8–5.1 (m, 2H, O=CH$_2$), 1.1–3.2 (m, 11H, CH$_3$, indane CH$_2$, and cyclopropane H).

EXAMPLE 4

Preparation of 2,2-Dimethyl-4,5-benzospiro[2,4]hepta-4-ene-1-carboxylic acid, α-cyano-m-phenoxybenzyl ester.

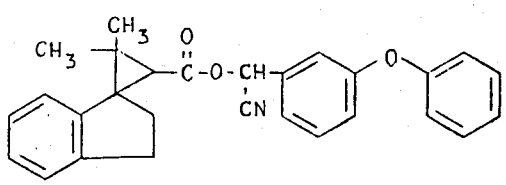

The procedure of Example 2 is followed using 2,2-dimethyl-4,5-benzospiro[2,4]hepta-4-ene-1-carboxylic acid in place of 2,2-dimethyl-4,5-benzospiro[2,4]hepta-4,6-diene-1-carboxylic acid to give the crude product.

EXAMPLE 5

Preparation of 2,2-Dimethylspiro[2,4]hepta-4,6-diene-1-carboxylic acid, m-phenoxybenzyl ester.

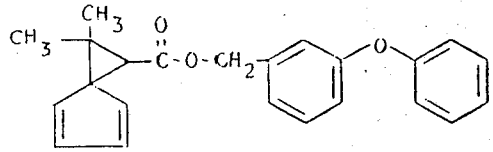

The procedure of Example 1 is followed using 2,2-dimethyl[2,4]hepta-4,6-diene-1-carboxylic acid in place of 2,2-dimethyl-4,5-benzospiro[2,4]hepta-4,6-diene-1-carboxylic acid to give the crude product.

EXAMPLE 6

Preparation of 2,2-Dimethylspiro[2,4]hepta-4,6-diene-1-carboxylic acid, α-cyano-m-phenoxybenzyl ester.

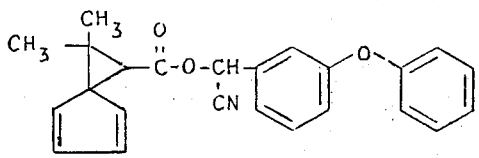

The procedure of Example 2 is followed using 2,2-dimethylspiro[2,4]hepta-4,6-diene-1-carboxylic acid in place of 2,2-dimethyl-4,5-benzospiro[2,4]hepta-4,6-diene-1-carboxylic acid to give the crude product.

EXAMPLE 7

Preparation of 2,2-dimethylspiro[2,4]heptane-1-carboxylic acid, m-phenoxybenzyl ester.

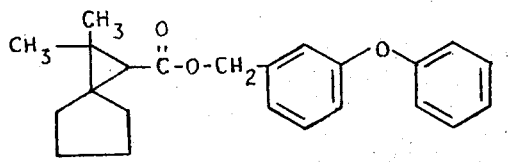

The procedure of Example 1 is followed using 2,2-dimethylspiro[2,4]heptane-1-carboxylic acid in place of 2,2-dimethyl-4,5-benzospiro[2,4]hepta-4,6-diene-1-carboxylic acid to give the crude product. The pure ester obtained by chromatography has the following spectral properties: Infrared spectrum (neat film) 1730 cm$^{-1}$; nuclear magnetic resonance spectrum (CCl$_4$) δ = 6.8–7.4 (m, 9H, aromatic), 5.0 (s, 2H, 0-CH$_2$), 1.4–1.7 (m, 8H, cyclopentane CH$_2$), 1.1 (s$_x$, 3H, CH$_3$), 1.2 (s, 3H, CH$_3$).

EXAMPLE 8

Preparation of 2,2-Dimethylspiro[2,4]heptane-1-carboxylic acid, α-cyano-m-phenoxybenzyl ester.

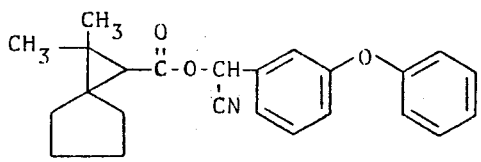

The procedure of Example 2 is followed using 2,2-dimethylspiro[2,4]heptane-1-carboxylic acid in place of 2,2-dimethyl-4,5-benzospiro[2,4]hepta-4,6-diene-1-carboxylic acid to give the crude product.

It must be recognized that various geometric isomers as well as optical isomers result from these preparations. Thus, in the case of the 2,2-dimethylspiro[2,4]-hepta-4,6-diene-1-carboxylic acid and 2,2-dimethylspiro[2,4]-heptane-1-carboxylic acid esters of m-phenoxybenzyl alcohol, d and l isomeric pairs will result. Where the α-cyano and α-ethynyl m-phenoxybenzyl esters are formed, an additional chiral center is introduced allowing for additional d, l pairs. Although in most instances the separation of these isomers may not be practical, it is recognized that they will differ in the degree of effectiveness and the spectrum of their activity against the many insects and other pests of economic importance. In addition, the subject esters derived from 2,2-dimethyl-4,5-benzospiro[2,4]hepta-4,6-diene-1-carboxylic acid and 2,2-dimethyl-4,5-benzospiro[2,4]-hepta-4-ene-1-carboxylic acid will be further complicated by the presence of cis and trans isomers. These different esters are also expected to show differing degrees of insecticidal activity when separately tested.

EXAMPLE 9

Preparation of 2,2-Dimethyl-4,5-benzospiro[2,4]hepta-4,6-diene-1-carboxylic acid, α-ethynyl-m-phenoxybenzyl ester.

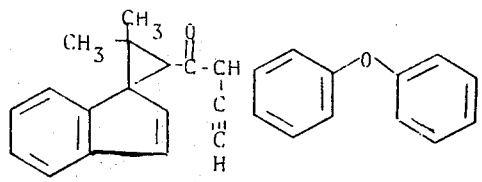

The procedure of Example 1 is followed using α-ethynyl-m-phenoxybenzyl alcohol in place of m-phenoxybenzyl alcohol to give the product as an oil.

EXAMPLE 10

Preparation of 2,2-Dimethyl-4,5-benzospiro[2,4]hepta-4-ene-1-carboxylic acid, α-ethynyl-m-phenoxybenzyl ester.

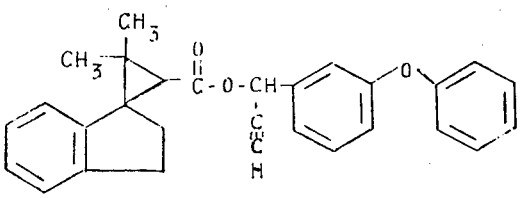

The procedure of Example 1 is followed using 2,2-dimethyl-4,5-benzospiro[2,4]hepta-4-ene-1-carboxylic acid in place of 2,2-dimethyl-4,5-benzospiro[2,4]hepta-4,6-diene 1-carboxylic acid and α-ethynyl-m-phenoxybenzyl alcohol in place of m-phenoxybenzyl alcohol to give the product as an oil.

EXAMPLE 11

Preparation of 2,2-Dimethylspiro[2,4]hepta-4,6-diene-1-carboxylic acid, α-ethynyl-m-phenoxybenzyl ester.

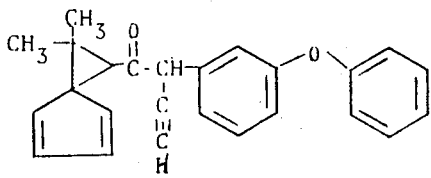

The procedure of Example 1 is followed using 2,2-dimethylspiro[2,4]hepta-4,6-diene-1-carboxylic acid in place of 2,2-dimethyl-4,5-benzospiro[2,4]hepta-4,6-diene-1-carboxylic acid and α-ethynyl-m-phenoxybenzyl alcohol in place of m-phenoxybenzyl alcohol to give the product as an oil.

EXAMPLE 12

Preparation of 2,2-Dimethylspiro[2,4]heptane-1-carboxylic acid, α-ethynyl-m-phenoxybenzyl ester

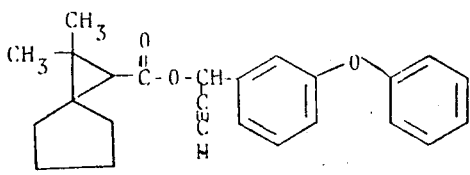

The procedure of Example 1 is followed using 2,2-dimethylspiro[2,4]heptane-1-carboxylic acid in place of 2,2 dimethyl-4,5-benzospiro[2,4]hepta-4,6-diene-1-carboxylic acid and α-ethynyl-m-phenoxybenzyl alcohol in place of m-phenoxybenzyl alcohol to give the product as an oil.

EXAMPLE 13

Insecticidal Activity

The high degree of effectiveness of the compounds of the invention for controlling insects is demonstrated in the following tests, wherein Tobacco budworm, *Heliothis virescens* (Fabricius); Cotton Boll Weevil, *Anthonomus grandis* (Boheman); Western Potato Leafhopper, *Empoasca abrupta* (Soy) and Bean Aphid, *Aphis fabae* (Scopoli), are employed as test insect species. Procedures employed are as follows: Tobacco Budworm, *Heliothis virescens* (Fabricius).

A cotton plant with two true leaves expanded is dipped for 3 seconds with agitation in a test solution (35% water/65% acetone) containing 300, 100 or 10 ppm of test compound. A ½ to ¾-inch square of cheesecloth with about 50 to 100 budworm eggs 0–24 hours old is also dipped in the test solution and placed on a leaf of the cotton plant, all being placed in the hood to dry. The leaf with the treated budworm eggs is removed from the plant and placed in an 8-ounce Dixie cup with a wet 2 inches piece of dental wick and covered with a lid. The other leaf is placed in a similar cup with a wick and a piece of cheesecloth infested with 50–100 newly hatched larvae is added before covering the cup with a lid. After 3 days at 80°F, 50% r.h., observations of egg hatch are made, as well as kill of newly hatched larvae. Data obtained are reported as percent kill in the table below. Cotton Boll Weevil, *Anthonomus grandis* (Boheman).

A cotton plant with cotyledons expanded is dipped for 3 seconds, with agitation, in a 35% water/65% acetone solution containing 1000 ppm of test compound. The dipped plants are then placed in a hood to dry. One cotyledon is removed from the plant and placed in a 4-inch petri dish containing a moist filter paper on the bottom and 10 adult boll weevils. After 2 days at 80°F, and 50% r.h., mortality counts are made. Data obtained are reported below.

Western Potato Leafhopper, *Empoasca abrupta* (Soy).

A Sieve lima bean plant with the primary leaf expanded to 3 to 4 inches is dipped into a 35% water/65% acetone solution containing 100 ppm of test compound. The dipped plant is placed in the hood to dry and then a one-inch piece of the tip of one leaf is cut off and placed in a 4-inch petri dish with a moist filter paper in the bottom. From 3 to 10 second-instar nymphs are placed in the dish and the dish is then covered. Mortality counts are made holding the thus-prepared dishes for 2 days at 80°F and 50% r.h.

Bean Aphid, *Aphis fabae* (Scopoli).

Two-inch fiber pots, each containing a nasturtium plant 2 inches high and infested with 100 to 150 aphids 2 days earlier are placed on a 4 rpm turntable and sprayed with a 35% water/65% acetone solution containing 100 ppm of test compound for 2 revolutions using a DeVilbiss Atomizer and 20 psi air pressure. The spray tip is held about 6 inches from the plants and the spray directed so as to give complete coverage of the aphids and the plants. The sprayed plants are laid on their sides on white enamel trays. Mortality estimates are made after 1 day at 70°F., 50% r.h.

In these tests, permethrin and phenothrin, known pyrethroid insecticides, are used as checks for the purpose of evaluation. Data are reported as percent mortality determined at the rate indicated. From the data it can be seen that the test compounds are substantially more effective than permethrin and phenothrin against the above-named insects.

| Compound ppm | Insecticidal Evaluation | | | | |
|---|---|---|---|---|---|
| | Tobacco Budworm | | Boll Weevil ppm 1000, 100 | Leaf Hopper ppm 100, 10 | Aphids 100, 10, 1, .1 |
| | Eggs ppm 300, 100, 10 | Larvae ppm 300, 100, 10 | | | |
| Cl$_2$C=CH—[cyclopropane with CH$_3$, CH$_3$]—CO-O-CH$_2$—[phenyl]—O—[phenyl]  Permethrin | 100, 100, 0 | 100, 100, 50 (RF) | 0, 0 (RF) (RF)<br>100 70<br>100 80<br>100 60 | 100, 0 | 100,100,100, 0 |
| CH$_3$, CH$_3$—[indane-cyclopropane]—CO-O-CH$_2$—[phenyl]—O—[phenyl] | 100, 100, 0 | 100, 100, 100 | 100, 0 (RF) | 100,100 | 100,100,100, 0 |
| CH$_3$, CH$_3$—[indane-cyclopropane]—CO-O-CH(CN)—[phenyl]—O—[phenyl] | 100, 100, 0 | 100, 100, 100 | 100, 0 (RF) | 100,100 | 100,100,100,100 |
| (CH$_3$)$_2$C=CH—[cyclopropane with CH$_3$, CH$_3$]—CO-O-CH$_2$—[phenyl]—O—[phenyl]  Phenothrin | 100, 100, 0 | 100, 100, 0 | 80, 0 | 100, 60 | 100,100,100, 0 |

RF = Reduced Feeding

EXAMPLE 14

Insecticidal Activity

The unique insecticidal activity of the phenoxybenzyl esters of spiro carboxylic acids of the present invention is demonstrated in the following tests wherein a variety of pyrethroid type insecticides are employed as controls. The confused Flour Bettle, *Tribolium confusum* and the German Cockroach, *Blattella germanica* are used for this evaluation.

Confused Flour Beetle - *Tribolium confusum*

The compounds to be tested are formulated at 1% dusts by mixing 0.1 cc (0.1 ml if a liquid) with 9.9 cc of Pyrax ABB talcs, wetting with 5 ml of acetone, and grinding to dryness in a mortar and pestle. 12.5 Milligrams of this dust is blown into the top of a dust settling tower with a short blast of air at 20 psi, and allowed to settle for 2 minutes on 9 cm petri dishes. (Deposit = .09375 mg/cm$^2$ of 1% dust). 25 Adult confused Flour Beetles are placed in each dish. Mortality counts are made after 3 days at 80°F. A beetle is "alive" if it can move 2 or more appendages when prodded.

German Cockroach — *Blattella germanica.*

The compounds to be tested are formulated as 1% dusts as described above in the test procedure for the confused Flour Beetle. 25 Milligrams of the dust is sprinkled manually over the bottom of a 7½ inch diameter dish 2½ inches high. A water bottle with cotton wick is arranged to supply water to the test insects, and 10 male adult German Cockroaches are placed in the dish. A screen cover is placed over the dish to prevent the insects escape. Mortality counts are made after holding the prepared test dishes for 3 days at 80°F.

Data obtained are reported in the table below as percent insect mortality. From the data it can be seen that the compounds of this invention are highly effective insecticidal agents superior to non-halogenated pyrethroids known in the art, and as effective or superior to the halogenated pyrethroids of the art, against the insects mentioned above.

The term "pyrethrins" is used in the following table and means a mixture of 4 compounds Pyrethrin I and II and Cinerin I and II shown as follows:

Mixture of 4 Compounds

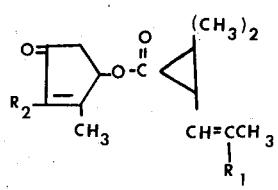

Pyrethrin I: C$_{21}$H$_{28}$O$_3$
R$_1$ = —CH$_3$

R$_2$ = —CH$_2$CH=CHCH=CH$_2$
Cinerin I: C$_{20}$H$_{28}$O$_3$
R$_1$ = —CH$_3$

R$_2$ = —CH$_2$CH=CHCH$_3$

Pyrethrin II: C$_{22}$H$_{28}$O$_5$
R$_1$ = —C(=O)—OCH$_3$

R$_2$ = —CH$_2$CH=CHCH=CH$_2$
Cinerin II: C$_{21}$H$_{28}$O$_5$
R$_1$ = —C(=O)—OCH$_3$

R$_2$ = —CH$_2$CH=CHCH$_3$

| | Compound | | Insecticidal Activity* % Kill-Tribolium At | | % Kill-German Roach At | |
|---|---|---|---|---|---|---|
| | | | 1% | 0.1% | 1% | 0.1% |
| 1 | Allethrin | cis-trans-±)-2,2-dimethyl-3-(2-methylpropenyl)cyclo-propanecarboxylic acid, (±)-2-allyl-4-hydroxy-3-methyl-2-cyclopenten-1-one ester | 0 | — | 100 | — |
| 2 | Barthrin | cis-trans-(±)-2,2-dimethyl-3-(2-methylpropenyl)cyclo-propanecarboxylic acid, 6-chloropiperonyl ester | 0 | — | 0 | — |
| 3 | | Prethrins(mixture of Pyrethrin I and II and Cinerin I and II) | 4 | — | 100 | 15 |
| 4 | Resmethrin | cis-trans-(±)-2-2-dimethyl-3-(2-methylpropenyl)cyclo-propanecarboxylic acid, (5-benzyl-3-furyl)methyl ester | 100 | 8 | 100 | 80 |
| 5 | Permethrin | cis-trans-(±)-3-(2,2-di-chlorovinyl)-2,2-dimethyl-cyclopropane carboxylic acid, m-phenoxybenzyl ester | 100 | 24** | 100 | 100 |
| 6 | Phenothrin | cis-trans-(±)-2,2-di-methyl-3-(2-methyl-propenyl)cyclopropane-carboxylic acid, m-phen-oxybenzyl ester | 100 | 8** | 100 | 100 |
| 7 | | 2,2-Dimethyl-4,5-benzo-spiro[2,4]-hepta-4,6-diene-1-carboxylic acid, m-phenoxybenzyl ester | 100 | 20** | 100 | 100 |
| 8 | | 2,2-Dimethyl-4,5-benzo-spiro[2,4]-hepta-4,6-diene-1-carboxylic acid, α-cyano-m-phenoxybenzyl ester | 100 | 100** | 100 | 100 |

*Art compounds 1–6
**Average two tests

EXAMPLE 15

Insecticidal Activity

The unique insecticidal activity of the compounds of the present invention, over a variety of pyrethroid type insecticides, is further demonstrated by the following tests.

The test procedures employed for evaluation against Boll weevils, Southern Armyworms and Tobacco Budworms are described in the preceeding examples. The procedures employed for evaluation against mosquito larvae and Mexican Bean Beetles are as follows.

Malaria Mosquito — Anopheles quodrimaculatus Say

1 Milliter of a 35% water/65% acetone solution containing 300 ppm of test compound is pipetted in a 400 ml beaker containing 250 ml of deionized water and stirred with the pipette, giving a concentration of 1.2 ppm. A wax paper ring one-fourth inch wide to fit inside the beaker is floated on the surface of the test solution to keep the eggs from floating up the meniscus curve and drying out on the side of the glass. A spoon made of screen is used to scoop up and transfer about 100 eggs (0–24 hours old) into the test beaker. After 2 days at 80°F., 50% r.h., observations of hatching are made.

Mexican Bean Beetle — Epilachna varivestis Mulsant

Sieva lima bean plants (2 per pot) with primary leaves 3 to 4 inches long, are dipped in the 300 ppm test solution and set in the hood to dry. One leaf is removed from a plant and placed in a 4 inch petri dish containing a moist filter paper on the bottom and 10 last-instar larvae (13 days from hatching). The day after treatment, another leaf is removed from the plant and fed to the larvae after removing the remains of the original leaf. Two days after treatment, the third leaf is fed to the larvae, this usually being the last needed. The fourth leaf is used on the third day after treatment if the larvae have not finished feeding. The test is now set aside and held until adults have emerged, usually in about 9 days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Data obtained are reported in the table below.

Southern Armyworm — Spodaptera eridania (Cramer) Methods:

Sieva lima bean plants pruned back to two expanded 3 to 4 inchesprimary leaves are dipped three seconds with agitation in the treatment solutions and then set in a hood to dry. After the leaves are dry they are excised and each excised leaf is placed in a 4 inch petri dish containing a piece of moist filter paper and ten third-instar southern armyworm larvae approximately three-eighths of an inch long. The petri dishes are covered and placed in a holding room for 2 days at a temperature of 80°F and 50% relative humidity.

Mortality counts are made after 2 days. Compounds which produce a larval kill are held for an extra day and counted again.

| Compound | Insecticidal Activity | | | | | | | | | | |
|---|---|---|---|---|---|---|---|---|---|---|---|
| | Mosquito Larvae ppm | | | | Boll Weevil ppm | Southern Armyworms ppm | | Mexican Bean Beetles ppm | | Tobacco Budworm ppm | |
| | 1.2 | .4 | .04 | .004 | 1000 | 1000 | 100 | 10 | 300 | 100 | 1000 | 100 |
| [structure: CH₃, CH₃, CN, CO-OCH-, indane, phenoxyphenyl] | 100 | 100 | 100 | 100 | 100 | 100 | 100 | 100 | 100 | 100 | 100 | 100 |
| [structure: CH₃, CH₃, CO-OCH₂-, indane, phenoxyphenyl] | — | 100 | 100 | — | 30 | 100 | 100 | 0 | — | — | 100 | 80 |
| [structure: CH₃, CH₃, CO-OCH₂-, indane, phenoxyphenyl] | 100 | 100 | 100 | 50 | 100 | 100 | 100 | 90 | 100 | 90 | 100 | 100 |

— = No Test

EXAMPLE 16

Residual Insecticidal Activity
Leaf Dip Test

Young cotton plants with 2 or 3 expanded true leaves an dipped into 65% acetone-water solutions to thoroughly wet the leaves. The leaves are allowed to dry before the initial leaf samples are removed for bioassay with southern armyworm, *Prodenia eridania* (Cramer), tobacco budworm, *Heliothis virescens* (Fabricius) or cabbage looper, *Trichoplusia ni* (Hübner). Leaf samples are placed in a standard glass petri dish containing moist filter paper and 10 third instar southern armyworm or cabbage loopers. For the tobacco budworm assay, a single leaf is cut into sections of about one-half square inch and placed in individual medicine cups with a moist dental wick and one tobacco budworm larvae. The assay samples are held at a constant temperature of 80°F for 72 hours when mortality counts are made and the corrected percent mortality determined.

The treatment solutions are prepared by dissolving 100 mg of test compound in 65 ml of acetone then making the solution to 100 ml with deionized water to give a 1000 ppm concentration of the compound. Ten fold dilutions are prepared by taking 10 ml of the 1000 ppm solution and diluting to 100 ml with 65% acetone and water for 100 ppm. Then 10 ml of the 100 ppm solution is diluted the same way to give a 10 ppm solution.

After the leaves have dried the plants are removed to the greenhouse section fitted with polymethyl methacrylate panels which permit the penetration of ultraviolet light for determination of the residual insecticidal persistance of the compound. Leaf samples are removed for bioassay over a 9-to 10-day period.

Data obtained are reported in the table below where it can be seen that the compounds of the present invention are highly effective as insecticidal agents for an extended period of time when applied to plants as a liquid formulation containing from about 100 ppm to 1000 ppm of active compound.

Residual Insecticidal Activity
Percent Corrected Mortality

| Compound | Conc. (ppm) | 0 Days | | | 7 Days | | | 9 Days | | | 10 Days | | |
|---|---|---|---|---|---|---|---|---|---|---|---|---|---|
| | | Cabbage Looper | SAW | TBW | Cabbage Looper | SAW | TBW | Cabbage Looper | SAW | TBW | Cabbage Looper | SAW | TBW |
| 2,2-Dimethyl-4,5-benzo-spiro[2,4]hepta-4,6-diene 1-carboxylic acid, m phenoxybenyl ester | 1000 | 100 | 100 | 100 | 100 | 100 | 100 | 100 | 100 | 80 | | | |
| | 100 | 100 | 100 | 100 | 60 | 50 | 20 | 75 | 38 | 40 | | | |
| 2,2-Dimethyl-4,5-benzo-spiro[2,4]hepta-4,6-diene 1-carboxylic acid, α-cyano-m-phenoxybenzyl ester | 1000 | 100 | 100 | | 100 | 100 | | | | | 100 | 80 | |
| | 100 | 100 | 80 | | 70 | 80 | | | | | 90 | 20 | |

SAW = Southern Armyworm
TBW = Tobacco Budworm

EXAMPLE 17

Residual Insecticidal Activity
Foliar Spray Test

Young cotton plants with 3 to 4 expanded true leaves and young bean plants are sprayed with an overhead traveling spray apparatus delivering 86 gallons of liquid per acre through a flat fan nozzle. By varying the compound concentration in the spray solution different rates of compound per acre are obtained; hence 84 mg of compound per 240 ml of solution will result in the delivery of 4 oz of compound in 86 gallons of liquid per acre, 42 mg per 240 ml of solution will result in the delivery of 2 oz of compound in 86 gallons of liquid per acre and 21 mg per 240 ml of solution will result in 1 oz of compound in 86 gallons of liquid per acre.

Plants are sprayed and leaves permitted to dry before initial leaf samples are taken for bioassay with southern armyworm and tobacco budworm. Bioassay is done as described for Leaf Dip Test.

Plants are removed to the greenhouse for evaluation of residual persistance of the compounds as described for Leaf Dip Test.

Solutions are prepared by dissolving 84 mg of compound in 240 ml of 65% acetone-water (A) for the 4 oz/A rate, 120 ml of solution A is diluted to 240 ml with 65% acetone-water (B) for the 2 oz/A rate, and 120 ml of solution B is diluted to 240 ml with 65% acetone-water for the 1 oz/A rate. To each 120 ml of spray solution is added 0.2 ml of 3% Triton X-100 surfactant.

Data obtained are reported in the table below where it can be seen that the compounds of the present invention demonstrate unusual residual insecticidal effectiveness as compared to a variety of the known pyrethroid type insecticidal compounds. Only the chlorinated art compound "permethrin" [cyclopropane carboxylic acid, 3-(2,2-dichlorovinyl)-2,2-dimethyl-m-phenoxybenzyl ester] of all pyrethroid types tested, also exhibited extended residual activity.

1 oz = 28.35 grams
2 oz = 56.70 grams
4 oz = 113.40 grams is then diluted to 10 ml with acetone to make solution B; and 1 ml of said solution B is further diluted to 10 ml with acetone to make solution G. Approximately 0.7 g Pyrax ABB talc is then placed in a 1 oz wide-mouth jar and 1.25 ml of the selected solution is added to the talc to produce the following concentrations:

1.25 ml solution A yields 50 lb/A
1.25 ml solution B yields 10 lb/A
1.25 ml solution C yields 1 lb/A The selected test solution is mixed with the talc to wet it evenly before it is dried under an air-jet dryer for 10–15 minutes. Twenty-five ml of moist sterilized potting soil and approximately 0.6 g millet seed (food for larvae) are then added to the jars containing test compound. The jars are capped and the contents mixed on a vibrating mixer. Each jar then receives 10 Southern corn rootworm larvae 6–8 days old. The jars are loosely capped and placed in a holding room at 80°F and 50% r.h. with constant light. Mortality counts are made after 6 days.

From the data obtained and reported below, as percent mortality, it can be seen that the m-phenoxybenzyl esters of spirocarboxylic acids of the present invention are highly effective soil insecticidal agents, when applied to soil at a rate of from 10 pounds to 50 pounds per acre.

| Soil Insecticide Activity | | |
|---|---|---|
| | Southern Corn Rootworm | |
| Compound | 50 lb/A | 10 lb/A |
| 2,2-Dimethyl-4,5-benzospiro-[2,4]hepta-4,6-diene-1-carboxylic acid, m-phenoxybenzyl ester | 100 | 0 |
| 2,2-Dimethyl-4,5-benzospiro-[2,4]hepta-4,6-diene-1-carboxylic acid, α-cyano-m-phenoxybenzyl ester | 100 | 100 |

Residual Insecticidal Activity
Percent Mortality

| Compound | Rate/A | 0 Days SAW | 0 Days TBW | 4 Days SAW | 4 Days TBW | 6 Days SAW | 6 Days TBW | 11 Days SAW | 11 Days TBW |
|---|---|---|---|---|---|---|---|---|---|
| Cyclopropanecarboxylic acid, 2,2-dichloro-3,3-dimethyl-, α-cyano-m-phenoxybenzyl ester | 1 oz | 0 | 50 | 0 | 0 | — | — | — | — |
| | 2 oz | 100 | 100 | 20 | 20 | 50 | 70 | 10 | 70 | — | — | 0 | 90 | — | — |
| | 4 oz | 100 | 100 | 60 | 0 | 25 | 90 | 0 | 40 | 100 | 90 | 20 | 0 | 90 | 100 | 0 | 20 |
| Butyric acid, 3-methyl-2-p-tolyl-, m-phenoxybenzyl ester | 1 oz | 0 | 100 | 0 | 20 | 60 | 70 | 20 | 20 | 0 | 10 | 20 | 0 | 0 | 10 | 0 | 0 |
| | 2 oz | 100 | 70 | 40 | 0 | 90 | 70 | 100 | 25 | 90 | 100 | 40 | 60 | 20 | 70 | 60 | 60 |
| | 4 oz | 100 | 100 | 100 | 80 | 100 | 100 | 80 | 60 | 100 | 100 | 100 | 100 | 100 | 100 | 20 | 40 |
| 2,2-Dimethyl-4,5-benzospiro-[2,4]hepta-4,6-diene-1-carboxylic acid, m-phenoxybenzyl ester | 1 oz | 100 | 100 | 40 | 40 | 80 | 90 | 80 | 60 | 50 | 70 | 40 | 60 | 60 | 100 | 0 | 0 |
| | 2 oz | 100 | 100 | 100 | 100 | 90 | 100 | 40 | 80 | 100 | 100 | 100 | 100 | 90 | 60 | 40 | 0 |
| | 4 oz | 100 | 100 | 100 | 100 | 100 | 100 | 100 | 80 | 100 | 100 | 100 | 100 | 100 | 100 | 80 | 80 |
| 2,2-Dimethyl-4,5-benzospiro-[2,4]hepta-4,6-diene-1-carboxylic acid, α-cyano-m-phenoxybenzyl ester | 1 oz | 100 | 100 | 40 | 0 | 100 | 100 | 60 | 20 | 100 | 90 | 100 | 60 | 100 | 100 | 40 | 20 |
| | 2 oz | 100 | 100 | 60 | 100 | 100 | 100 | 100 | 80 | 100 | 100 | 100 | 60 | 100 | 100 | 0 | 20 |
| | 4 oz | 100 | 100 | 100 | 60 | 100 | 100 | 60 | 100 | 100 | 100 | 100 | 80 | 100 | 100 | 20 | 40 |
| Cyclopropanecarboxylic acid, 3-(2,2-dichlorvinyl)-2,2-dimethyl-,m-phenoxybenzyl ester, trans and cis | 1 oz | 100 | 100 | 100 | 80 | 100 | 100 | 40 | 100 | 100 | 100 | 60 | 80 | 100 | 100 | 80 | 100 |
| | 2 oz | 100 | 100 | 100 | 100 | 100 | 100 | 100 | 100 | 100 | 100 | 100 | 100 | 100 | 100 | 80 | 60 |
| | 4 oz | 100 | 100 | 100 | 100 | 100 | 100 | 100 | 100 | 100 | 100 | 100 | 100 | 100 | 100 | 80 | 100 |
| Cyclopropanecarboxylic acid, 2,2-dimethyl-3-(2-methyl-propenyl)-3-phenoxybenzyl ester | 1 oz | 100 | 100 | 40 | 80 | 0 | 0 | 0 | 0 | 0 | 0 | 20 | 0 | 0 | 0 | 0 | 0 |
| | 2 oz | 100 | 100 | 100 | 40 | 100 | 80 | 40 | 40 | 50 | 80 | 20 | 0 | 0 | 0 | 0 | 0 |
| | 4 oz | 100 | 100 | 80 | 60 | 100 | 100 | 100 | 100 | 100 | 100 | 20 | 0 | 0 | 0 | 0 | 0 |

Art Compounds 1 – 3 and 6 – 7.
SAW = Southern Armyworm
TBW = Tobacco Budworm

EXAMPLE 18

Soil Insecticidal Activity.
Southern Corn Rootworm — Diabrotica undecimpunctata howardi (Barber)

Ten mg of compound are diluted to 10 ml with acetone to make a stock solution. Two ml of this solution

EXAMPLE 19

Systemic Control of Stable Flies on Mice.
α-Cyano-m-phenoxybenzyl ester of 2,2-dimethyl-4,5-benzospiro[2,4]hepta-4,6-diene-1-carboxylic acid is dissolved in 10% acetone/90% corn oil and administered orally (by gavage) to two 20 g Swiss-Webster white female mice at 400 mg/kg. One mouse is dosed with 10% acetone/90% corn oil and used as a control.

One hour after treatment, 9 stable flies (*Stomoxys calcitrans*) are placed in a cage with each mouse and allowed 4½ hours to feed. Within 1½ hours after the flies are placed with the mice, all flies in the treated group are "knocked down". The flies are held overnight and mortality measured at 24 hours.

| Number Mice Treated | Dose (mg/kg) | Number Flies on | Number Dead After 24 Hours |
|---|---|---|---|
| 2 | 400 | 18 | 17 |
| 1 | 0 | 9 | 2 |

EXAMPLE 20

Animal Systemic Insecticidal Activity

To determine the effectiveness of the compounds of the invention as animal insecticidal agents, the m-phenoxybenzyl ester of 2,2-dimethyl-4,5-benzospiro[2,4]-hepta-4,6-diene-1-carboxylic acid; and the α-cyano-m-phenoxybenzyl ester of 2,2-dimethyl-4,5-benzospiro[2,4]hepta-4,6-diene 1-carboxylic acid are mixed in 10% acetone-90% sesame oil and administered by gavage to 2 mice each at 25, 100, 200 and 400 mg/kg of animal body weight.

Adult, one day old, unfed stable flies *Stomoxys calcitrans* are then exposed to the mice for 18 hours to permit them to feed on said mice. Mortality counts are made at 24 hours and data obtained are reported below:

| Compound | No. Mice Treated | Dose mg/kg | No. Flies | No. of Dead Flies |
|---|---|---|---|---|
| 2,2-Dimethyl-4,5-benzo-spiro[2,4]hepta-4,6-diene-1-carboxylic acid, m-phenoxybenzyl ester | 2 | 400 | 20 | 20 |
|  | 2 | 200 | 20 | 20 |
|  | 2 | 100 | 20 | 10 |
|  | 2 | 25 | 20 | 2 |
|  | 2 | 0 | 20 | 0 |
| 2,2-Dimethyl-4,5-benzo-spiro[2,4]hepta-4,6-diene-1-carboxylic acid, α-cyano-m-phenoxybenzyl ester | 2 | 400 | 20 | 20 |
|  | 2 | 200 | 20 | 20 |
|  | 2 | 100 | 20 | 20 |
|  | 2 | 25 | 20 | 9 |
|  | 2 | 0 | 20 | 0 |

EXAMPLE 21

Ixodicidal Activity

Effective control of acarina larvae is demonstrated in the following tests with larvae of *Boophilus microplus*, a one-host tick which can remain on a single host through its three life stages, i.e., larvae, nymph and adult. In these tests, a 10% acetone - 90% water mixture contains 3.1, 12.5 or 50 ppm of test compound. Twenty larvae are enclosed in a pipet sealed at one end with a gauze material and solution containing the test compound is then drawn through the pipet with a vacuum hose, the whole simulating a spray system. The ticks are then held for 48 hours at room temperature and mortality is determined. The results achieved are set forth below.

| Compound | % Mortality *Boophilus microplus* larvae |
|---|---|
| 2,2-Dimethyl-4,5-benzo-spiro[2,4]hepta-4,6-diene-1-carboxylic acid, m-phenoxybenzyl ester | 100% at 50 ppm<br>100% at 12.5 ppm<br>100% at 3.1 ppm |
| 2,2-Dimethyl-4,5-benzo-spiro[2,4]hepta-4,6-diene-1-carboxylic acid, α-cyano-m-phenoxybenzyl ester | 100% at 50 ppm<br>100% at 12.5 ppm<br>80% at 3.1 ppm |

We claim:
1. A compound having the formula

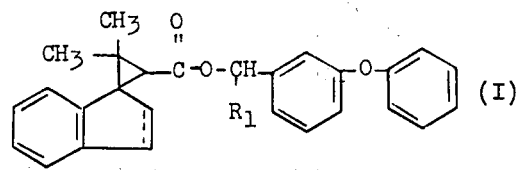

wherein $R_1$ is hydrogen, cyano or ethynyl, and $\rlap{=}=$ represents a single or double bond, and the optical and geometric isomers thereof.

2. A compound according to claim 1, wherein the compound has the structure:

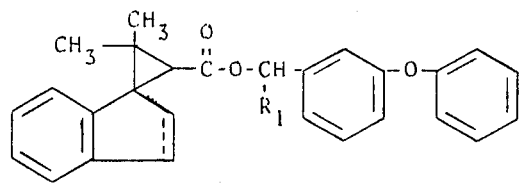

wherein $R_1$ and $\rlap{=}=$ are as described, and the stereoisomers thereof.

3. A compound according to claim 2 2,2-dimethyl-4,5-benzospiro[2,4]hepta-4,6-diene-1-carboxylic acid, m-phenoxybenxyl ester 4. A compound according to claim 2 2,2-dimethyl-4,5-benzospiro[2,4]hepta-4,6-diene-1-carboxylic acid, α-cyano-m-phenoxybenzyl ester.

5. A compound according to claim 2 2,2-dimethyl-4,5-benzospiro[2,4]hepta-4-ene-1-carboxylic acid, m-phenoxybenzyl ester.

6. A compound according to claim 2 2,2-dimethyl-4,5-benzospiro[2,4]hepta-4-ene-1-carboxylic acid, α-cyano-m-phenoxybenzyl ester.

7. A compound according to claim 2 2,2-dimethyl-4,5-benzospiro[2,4]hepta-4-ene-1-carboxylic acid, α-ethynyl-m-phenoxybenzyl ester.

8. A compound according to claim 2 2,2-dimethyl-4,5-benzospiro[2,4]hepta-4,6-diene-1-carboxylic acid, α-ethynyl-m-phenoxybenzyl ester.

9. A method for the control of insects and acarina comprising contacting said insects and acarina, their habitat or their food supply with an insecticidal or acaricidal amount of a compound having the formula:

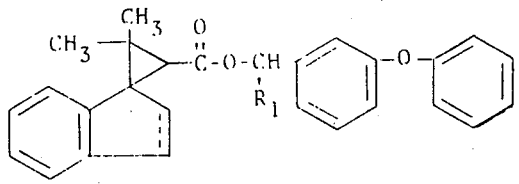

wherein $R_1$ is hydrogen, cyano or ethynyl, and $\rlap{=}-$ represents a single or double bond, and the optical and geometric isomers thereof.

10. A method according to claim 9, wherein the compound has the formula:

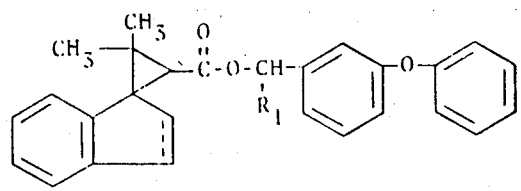

wherein $R_1$ is hydrogen, cyano or ethynyl, $\rlap{=}-$ is a single or double bond, and the stereoisomers of the compounds.

11. A method according to claim 10, wherein the compound is 2,2-dimethyl-4,5-benzospiro[2,4]hepta-4,6-diene-1-carboxylic acid, α-cyano-m-phenoxybenzyl ester.

12. A method according to claim 10, wherein the compound is 2,2-dimethyl-4,5-benzospiro[2,4]-hepta-4,6-diene-1-carboxylic acid, m-phenoxybenzyl ester.

13. A method for protecting plants from attack by insects comprising, applying to the foliage of the plants or to the soil in which they are growing, an insecticidally effective amount of a compound of the formula:

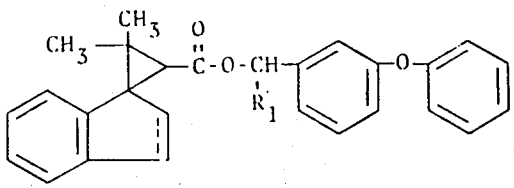

wherein $R_1$ is hydrogen, cyano or ethynyl, and $\rlap{=}-$ is a single or double bond, and the stereoisomers of the compounds.

14. A method according to claim 13, comprising applying the compound to the foliage of the plants in sufficient amount to provide from about 28 g to 228 g per acre of said compound.

15. A method according to claim 14, wherein the compound is applied at a rate of from 28 g to 113.4 g per acre.

16. A method according to claim 13 wherein the compound is applied to the soil in which plants are growing at a rate of from 10 to 50 pounds per acre.

* * * * *